United States Patent
Kawashima et al.

(10) Patent No.: US 6,280,982 B1
(45) Date of Patent: Aug. 28, 2001

(54) PROCESS FOR PRODUCTION OF DIHOMO-γ-LINOLENIC ACID AND LIPID CONTAINING SAME

(75) Inventors: Hiroshi Kawashima; Kengo Akimoto, both of Ibaraki; Hideaki Yamada; Sakayu Shimizu, both of Kyoto, all of (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 08/230,879

(22) Filed: Apr. 20, 1994

Related U.S. Application Data

(63) Continuation of application No. 07/953,096, filed on Sep. 29, 1992, now abandoned.

(30) Foreign Application Priority Data

Sep. 30, 1991 (JP) .................................... 3-251964

(51) Int. Cl.$^7$ ...................................... C12P 7/64
(52) U.S. Cl. ...................... 435/134; 435/136; 435/187
(58) Field of Search ................... 435/134, 136, 435/187

(56) References Cited

U.S. PATENT DOCUMENTS

| | | | |
|---|---|---|---|
| 4,916,066 | * 4/1990 | Akimoto et al. | 435/134 |
| 5,034,321 | 7/1991 | Nakajima et al. | 435/134 |
| 5,093,249 | 3/1992 | Nakajima et al. | 435/135 |

FOREIGN PATENT DOCUMENTS

| | | | |
|---|---|---|---|
| 0 273 708 | 12/1987 | (EP) . | |
| 0 332 423 | 3/1989 | (EP) . | |
| 0322227 | * 6/1989 | (EP) | 435/134 |
| 0 322 227 | 6/1989 | (EP) | 7/64 |
| 0399494 | * 11/1990 | (EP) | 435/134 |
| 0 399 494 | 11/1990 | (EP) | 7/64 |
| 63-14696 | 1/1988 | (JP) . | |
| 64-47384 | 2/1989 | (JP) . | |
| 64-47385 | 2/1989 | (JP) . | |
| 1-243992 | 9/1989 | (JP) . | |
| 2268690 | * 11/1990 | (JP) | 435/134 |
| 2-268690 | 11/1990 | (JP) . | |
| 3-49688 | 3/1991 | (JP) . | |
| 3-72892 | 3/1991 | (JP) . | |

OTHER PUBLICATIONS

Patent Abstracts of Japan, unexamined applns. c field, vol. 15, No. 231, Jun. 12, 1991 The Patent Office Japanese Govt., p. 148 C 840 No. 3–72 892 (Idemitsu Petrochem.)

R.J. Pollero, et al, "Biosynthetic transformations of the eicosa–8, 11 dienoic acid in *Acanthamoeba castellanii*", *Chemical Abstracts*, vol. 89, No. 23, Dec. 4, 1978, p. 293, 89: 193584n.

\* cited by examiner

*Primary Examiner*—Leon B. Lankford, Jr.
(74) *Attorney, Agent, or Firm*—Burns, Doane, Swecker & Mathis, L.L.P.

(57) ABSTRACT

A process for the production of dihomo-γ-linolenic acid comprising the steps of culturing a microorganism having an ability to produce araquidonic acid and having a reduced or lost Δ5 desaturase activity to produce dihomo-γ-linolenic acid or a lipid containing dihomo-γ-linolenic acid, and recovering the dihomo-γ-linolenic acid.

28 Claims, No Drawings

PROCESS FOR PRODUCTION OF DIHOMO-γ-LINOLENIC ACID AND LIPID CONTAINING SAME

This application is a continuation, of application Ser. No. 07/953,096, filed Sep. 29, 1992, abandoned.

BACKGROUND OF THE INVENTION

1. Field of the Invention

The present invention relates to a process for the production of dihomo-γ-linolenic acid (DGLA) and a lipid containing DGLA by fermentation using a microorganism capable of producing arachidonic acid (ARA) and having reduced or lost Δ5 desaturation activity.

2. Related Art

DGLA, also known as 8,11,14-eicosatrienoic acid, is known to be present as a constituent fatty acid of fish oils and seaweeds. However, because of the low content of DGLA in fish oils and the like, a purified DGLA product obtained from fish oils and seaweeds is expensive. As relatively efficient production processes, there are fermentation methods using a microorganism capable of producing DGLA (Japanese Unexamined Patent Publication No. 63-14696), methods providing enhanced productivity by adding an additive, such as an unsaturated fatty acid (Japanese Unexamined Patent Publication Nos. 64-47384, and 64-47385), and methods using sesame oil, one of various plant extracts, sesamin, episesamin or the like (Japanese Unexamined Patent Publication Nos. 1-243992, 2-268690, 3-72892 and 3-49688).

Various studies have been carried out regarding the actions of essential fatty acids on an organism, and it is known that in many cases eicosanoids derived from DGLA and ARA are antagonistic. Although it is known that a group of prostaglandin 1 group derived from DGLA exhibit platelet anti-coagulation action, vasodilation activity, bronchdilation activity anti-inflammatory action, and the like, for DGLA orally taken as a fat or oil in foods so as to exhibit the above-mentioned actions, DGLA-containing oil or fat product that has a low content of ARA antagonistic to DGLA is most preferable. Moreover, in the case wherein DGLA is purified from a DGLA-containing fat or oil, a DGLA-containing fat or oil having a low content of ARA is preferable as a starting material. Thus, the development of DGLA-containing fat or oil having a low content of ARA is in urgent demand, but a process for the production of such a fat or oil is not known.

SUMMARY OF THE INVENTION

Accordingly, the present invention provides a process for the production of DGLA and a lipid containing DGLA in a simple and efficient manner using a conventional inexpensive medium, and a process for the production of a lipid containing DGLA having a low content of ARA by adding an additive such as a Δ5 desaturase inhibitor.

The present invention have found that DGLA, which is a precursor of ARA, accumulates in a large amount when a microorganism capable of producing ARA and having reduced or lost Δ5 desaturation activity is cultured in a conventional medium, and that a ratio of ARA is further decreased and a ratio of DGLA is further increased when said microorganism is cultured in a medium supplemented with a Δ5 desaturation inhibitor.

Accordingly, the present invention provides a process for the production of DGLA comprising the steps of:

culturing a microorganism having an ability to produce ARA and having reduced or lost Δ5 desaturation activity in a medium to produce DGLA or a lipid containing DGLA; and recovering the DGLA.

The present invention also provides a process for the production of a lipid containing DGLA comprising the steps of:

culturing a microorganism having an ability to produce ARA and having reduced or lost Δ5 desaturation activity in a medium to produce a lipid containing DGLA; and recovering the lipid containing DGLA.

The present invention further provides a process for the production of DGLA comprising the steps of:

culturing a microorganism having an ability to produce ARA and having reduced or lost Δ5 desaturation activity in a medium supplemented with a Δ5 desaturase inhibitor, or adding a Δ5 desaturase inhibitor into a medium in which said microorganism has been cultured and further culturing the microorganism to produce DGLA or a lipid containing DGLA; and recovering the DGLA.

The present invention further provides a process for the production of a lipid containing DGLA comprising the steps of:

culturing a microorganism having an ability to produce ARA and having reduced or lost Δ5 desaturation activity in a medium supplemented with a Δ5 desaturase inhibitor, or adding a Δ5 desaturase inhibitor into a medium in which said microorganism has been cultured and further culturing the microorganism to produce a lipid containing DGLA; and recovering the lipid containing DGLA.

The present invention moreover provides a process for the production of DGLA comprising the steps of:

culturing a microorganism having an ability to produce ARA and having reduced or lost Δ5 desaturation activity in a medium supplemented with at least one additive selected from the group consisting of sesame oil, peanut oil, an extract obtained by extracting sesame oil with an organic solvent substantially immiscible with sesame oil, an extract of sesame seeds, an extract of Gokahi derived from a medicinal plant which is *Acanthopanax gracilistylus* W. W. Smith, *Acanthopanax senticosus* Harms, an extract of *Acanthopanax henryi*, or *Acanthopanax verticillatus* Hoo, an extract of Touboku derived from a medicinal plant, which is *Paulownia fortunei* Hemsl; or *Paulownia tomentosa* Steud., an extract of Hakukajihi derived from a medicinal plant, which is *Ginkgo biloba* L., which is Hihatsu derived from a medicinal plant, which is *Piper longum* L., an extract of Saishin (*Asiasari radix*) derived from a medicinal plant which is *Asiasarum heterotropoides* var. *mandshuricum*, or *Asarum sieboldii* Miq., an extract of tarragon, an extract of dill seeds, an extract of parsley, an extract of turmeric and an extract of nutmeg, or adding said additive into a medium in which said microorganism has been cultured and further culturing the microorganism to produce DGLA or a lipid containing DGLA, and recovering the DGLA.

The present invention further provides a process for the production of a lipid containing DGLA comprising the steps of:

culturing a microorganism having an ability to produce ARA and having reduced or lost Δ5 desaturation activity in a medium supplemented with at least one additive selected from the group consisting of sesame oil, peanut oil, an extract obtained by extracting sesame oil with an organic solvent substantially immiscible with sesame oil, an extract of sesame seeds, an extract of Gokahi derived from a medicinal plant, an extract of *Acanthopanax gracilistylus* W. W. Smith, an extract of *Acanthopanax senticosus* Harms, an extract of *Acanthopanax henryi*, an extract of *Acanthopanax verticillatus* Hoo, an extract of Touboku derived from a medicinal plant, an extract of *Paulownia fortunei* Hemsl; an extract of *Paulownia tomentosa* Steud., an extract of Hakukajihi derived from a medicinal plant, an extract of *Ginkgo biloba* L., an extract of Hihatsu derived from a medicinal plant, an extract of *Piper longum* L., an extract of Saishin (*Asiasari radix*) derived from medicinal plant, an extract of *Asiasarum heterotropoides* var. *mandshuricum*, an extract of *Asarum sieboldii* Miq., an extract of tarragon, an extract of dill seeds, an extract of parsley, an extract of turmeric and an extract of nutmeg, or adding said additive into a medium in which said microorganism has been cultured and further culturing the microorganism to produce a lipid containing DGLA, and recovering the lipid containing DGLA.

DETAILED DESCRIPTION

In the present invention any microorganisms having an ability to produce ARA and having reduced or lost Δ5 desaturase activity can be used. Microorganism having an ability to produce ARA include those belonging to the genus Mortierella, Conidiobolus, Pythium, Phytophthora, Penicillium, Cladosporium, Mucor, Fusarium, Asperaillus, Rhodotorula, or Entomophthora. As microorganisms belonging to the genus Mortierella, there are mentioned microorganisms belonging to the subgenus Mortierella, such as *Mortierella elongata, Mortierella exigua, Mortierella hygrophila, Mortierella alpina*, and the like. Microorganism used in the present invention, having an ability to produce ARA and having reduced or lost Δ5 desaturase activity can be obtained by mutating the microorganisms having an ability to produce ARA.

For mutagenesis, irradiation of a microorganism with a mutagen, such as radiation (X-ray, γ-ray, neutron or ultraviolet light), high temperature treatment, and chemical mutagens may be used. In a mutagenizing procedure, microbial cells are suspended to an appropriate buffer, and a mutagen is added therein. The treated suspension is incubated for an appropriate time, diluted and plated on a solid medium such as agar medium to form colonies of mutated microorganisms.

As chemical mutagens, alkylating agents such as nitrogen mustard, methyl methanesulfonate (MMS), N-methyl-N'-nitro-N-nitrosoguanidine (NTG); base analogs such as 5-bromouracil; antibiotics such as mitomycin C; base synthesis inhibitor such as 6-mercaptopurine; pigments such as proflavine; a certain carcinogens such as 4-nitroquinoline-N-oxide; and others such as manganese chloride, potassium permanganate, nitrous acid, hydrazine, hydroxylamine, formaldehyde, nitrofurane compounds may be mentioned. Microorganisms to be treated with a mutagen can be vegetative cells such as mycelium or spores.

As a mutant belonging to the genus Mortierella, *Mortierella alpina* SAM 1860 (FERM BP-3589) can be preferably used.

For culturing a mutant used in the present invention, spores, mycelium or a previously cultured precultur is inoculated to a liquid medium or solid medium. A liquid medium contains, as a carbon source, glucose, fructose, xylose, saccharose, maltose, soluble starch, molasses, glycerol, mannitol, and the like, alone or in combination.

As a nitrogen source, an organic nitrogen source such as peptone, yeast extract, malt extract, meat extract, casamino acids, corn steep liquor or urea, and an inorganic nitrogen source such as sodium nitrate, ammonium nitrate, ammonium sulfate or the like can be used alone or in combination. In addition, if necessary, inorganic salts such as phosphates, magnesium sulfate, ferric or ferrous sulfate, cupric sulfate or the like, and minor nutrient components such as vitamins may be used.

The concentration of components in a culture medium should be such that it does not inhibit the growth of microorganisms. Generally and practically, a concentration of carbon source is 0.1 to 30% by weight, preferably 1 to 10% by weight, and a concentration of nitrogen source is 0.01 to 5% by weight, and preferably 0.1 to 2% by weight. Temperature for culturing is 5 to 40° C., and preferably 20 to 30° C.; and a pH value of a medium is 4 to 10, and preferably 6 to 9. Culturing may be aeration/agitation culturing, shaking culture, or stationary culture. Culturing is usually continued for 2 to 10 days.

In the case wherein a microorganism is cultured in a solid medium, the medium comprises wheat bran, rice hulls, rice bran or the like supplemented with water in an amount of 50 to 100% by weight retuting to the weight of solid materials. Culturing is carried out at 5 to 40° C., preferably 20 to 30° C. for 3 to 14 days. In this case, the medium can contain nitrogen sources, inorganic salts, and minor nutrient compounds, such as those described above.

According to the present invention, to accelerate an accumulation of DGLA, a substrate of ARA can be added to a medium. As the substrates, hydrocarbons having 12 to 20 carbon atoms such as tetradecane, hexadecane and octadecane, fatty acid having 12 to 20 carbon atoms such as tetradecanoic acid, hexadecanoic acid and octodecanoic acid, a salts thereof, for example, sodium salt or potassium salt, fatty acid esters wherein the fatty acid moiety has 12 to 20 carbon atoms, for example, lower alkyl ester, for example, methyl ester, ethyl ester or propyl ester of such a fatty acid, and a lipid containing such fatty acids as its components, for example, olive oil, soybean oil, cotton seed oil, coconut oil may be mentioned, and they can be used alone or in combination.

Moreover, according to the present invention, to produce a lipid containing DGLA in which a content of ARA is decreased, a producer microorganism is cultured in the presence of a Δ5 desaturase inhibitor, resulting in the accumulation of a large amount of DGLA. In this case, as Δ5 desaturase inhibitors, there are mentioned dioxabicyclo [3.3.0]octane derivatives represented by the following formula (I):

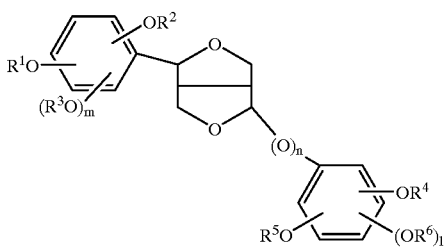

(I)

wherein $R^1$, $R^2$, $R^3$, $R^4$, $R^5$ and $R^6$ independently represent a hydrogen atom or an alkyl group having 1 to 3 carbon atoms, or $R^1$ and $R^2$, and/or $R^4$ and $R^5$ together form a methylene group or an ethylene group, and n, m and l are 0 or 1;

piperonyl butoxide, curcumin, and compounds represented by the following formula (II):

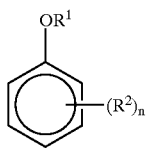

(II)

wherein $R^1$ represents a lower alkyl group; $R^2$ represents a hydroxyl group, an alkyl group, an alkoxy group, an alkenyl group or an oxyalkyl group wherein in the case that more than one $R^2$ is present, the $R^2$ may be the same or different, and n is an integer of 0 to 5. The lower alkyl group has 1 to 6 carbon atoms, for example, methyl, ethyl, n-propyl, isopropyl, n-butyl, isobutyl, tert-butyl and the like. The alkyl group, the alkyl moiety in the alkoxy group, or the oxyalkyl group, and the alkenyl group have 12 to 20 carbon atoms. The Δ5 desaturase inhibitors can be used alone or in combination.

As the dioxabicyclo[3.3.0]octane derivative, in the present invention, sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0] octane, 2,6-bis-(3-methoxy-4-hydroxyphenyl)-3,7-dioxabicyclo[3.3.0]octane or 2-(3,4-methylenedioxyphenyl)-6-(3-methoxy-4-hydroxyphenoxy)-3,7-dioxabicyclo[3.3.0]octane, for example, can be used. These derivatives can be used alone or in the form of a mixture of two or more thereof. Both the optically active form and racemic form can be used.

The dioxabicyclo[3.3.0]octane derivative, one of the Δ5 desaturase inhibitors of the present invention can be obtained by the following procedure. First, an extract composed mainly of the dioxabicyclo[3.3.0]octane derivatives can be obtained from sesame oil according to a method comprising extracting sesame oil with an organic solvent substantially immiscible with sesame oil and capable of extracting and dissolving the compound of the present invention, and concentrating the extract. As the organic solvent, there can be mentioned, for example, acetone, methylethylketone, diethylketone, methanol and ethanol. For example, an extract composed mainly of the compound of the present invention can be obtained by mixing sesame oil homogeneously with an organic solvent as mentioned above, allowing the mixture to stand at a low temperature, carrying out a phase separation according to a customary process, and removing the solvent from the solvent fraction by evaporation.

More specifically, sesame oil is dissolved in 2 to 10 volumes, preferably 6 to 8 volumes of acetone, and the solution is allowed to stand at −80° C. overnight. As a result, the oil component is precipitated, and the organic solvent is removed from the obtained filtrate by distillation, whereby an extract composed mainly of the compound of the present invention is obtained. Alternatively, sesame oil is mixed with hot methanol or hot ethanol, the mixture is allowed to stand at room temperature, and the solvent is removed from the solvent fraction to obtain an extract composed mainly of the compound of the present invention. More specifically, sesame oil is mixed with hot methanol (higher than 50° C.) or hot ethanol (higher than 50° C.) in a volume 2 to 10 times, preferably 5 to 7 times, as large as the volume of the sesame oil to effect a violent extraction. The phase separation is effected by a phase separation when standing at room temperature or a centrifugal separation according to customary procedures, and the solvent is removed from the solvent fraction by distillation to obtain an extract composed mainly of the compound used in the present invention. Furthermore, the supercritical gas extraction can be utilized.

The compound of the present invention can be obtained from an extract as mentioned above by treating the extract by a customary method such as column chromatography, high performance liquid chromatography, recrystallization, distillation, or liquid-liquid countercurrent distribution chromatography. More specifically, by using a reversed phase column ($5C_{18}$) and methanol/water (60/40) as the eluent, the extract is subjected to high performance liquid chromatography, the solvent is removed by distillation, and the obtained crystal is recrystallized from ethanol to obtain the compound used in the present invention, such as sesamin, episesamin, sesaminol or episesaminol. The sesame oil used in the present invention can be either a purified product or a crude product. Furthermore, sesame seeds or sesame lees (defatted sesame seeds having a residual oil content of 8 to 10%) can be used. In this case, sesame seeds or sesame lees are pulverized if necessary, and then subjected to the extraction according to customary procedures using any solvent, for example, a solvent as mentioned above with respect to the extraction from sesame oil. The extraction residue is separated, and the solvent is removed from the extract by evaporation or the like to obtain an extraction product.

The compound used in the present invention, for example, sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane or 2-(3,4-methylenedioxyphenyl)-6-(3-methoxy-4-hydroxyphenoxy)-3,7-dioxabicyclo[3.3.0]octane, can be obtained from a sesame seed extract, a sesame lee extract or a crude sesame oil extract according to the same procedures as described above. Moreover, the compound used in the present invention can be obtained from a by-product formed in the sesame oil-preparing process.

Note, sesamin obtained from *Asaiasari radix* exhibits the same effects as those provided by sesame seeds, sesame bran and sesame oil.

The process for the purification of the compound used in the present invention and the process for obtaining the extract are not limited to those mentioned above, and the compound used in the present invention and the extract composed mainly of the compound of the present invention are not limited to those obtained from sesame oil, sesame lees and sesame seeds, but as is apparent to persons with ordinary skill in the art, all natural substances containing the compound used in the present invention can be used. For example, there can be mentioned Gokahi derived from a medicinal plant which is *Acanthopanax gracilistylus* W. W. Smith, *Acanthopanax senticosus* Harms, *Acanthopanax henryi*, or *Acanthopanax verticillatus* Hoo, Touboku derived from a medicinal plant which is *Paulownia fortunei* Hemsl or *Paulownia tomentosa* Steud., Hakukajihi derived from a medicinal plant which is *Ginkgo biloba* L., Hihatsu derived from a medicinal plant which is *Piper longum* L., Saishin (*Asiasari radix*) derived from medicinal plant which is *Asiasarum heterotropoides* var. *mandshuricum* or *Asarum sieboldii* Miq.

The following processes can be adopted for the synthesis of the dioxabicyclo[3.3.0]octane derivative.

For example, sesamin and episesamin can be synthesized according to the process of Beroza et al. [J. Am. Chem. Soc., 78, 1242 (1956)]. Pinoresinol [in the general formula (I), $R^1$ and $R^4$ represent H, $R^2$ and $R^5$ represent $CH_3$, and n, m and l are zero] can be synthesized according to the process of Freundenberg et al. [Chem. Ber., 86, 1157 (1953)]. Furthermore, syringaresinol [in the general formula (I), $R^1$ and $R^4$ represent H, $R^2$, $R^3$, $R^5$ and $R^6$ represent $CH_3$, n is zero, and each of m and l is 1] can be synthesized according to the process of Freundenberg et al. [Chem. Ber., 88, 16 (1955)].

The compound used in the present invention also can be used in the form of a glycoside, to accelerate absorption as far as the glycoside has a specific Δ5 desaturase inhibitory activity.

As embodiments of the compound represented by the formula (II), anisole, methoxyphenol, dimethoxybenzene, diethoxybenzene, trimethoxybenzene, methoxytoluene, 3(2)-tert-butyl-4-hydroxanisole (BHA), eugenol, and the like can be mentioned.

Moreover, as additives added to a culture medium to increase an accumulation of DGLA, sesame oil, peanut oil, an extract obtained by extracting sesame oil with an organic solvent substantially immiscible in sesame oil, an extract of sesame seeds, an extract of Gokahi derived from a medicinal plant, an extract of *Acanthopanax gracilistylus* W. W. Smith, an extract of *Acanthopanax senticosus* Harms, an extract of *Acanthopanax henryi*, an extract of *Acanthopanax verticillatus* Hoo, an extract of Touboku derived from a medicinal plant, an extract of *Paulownia fortunei* Hemsl; an extract of *Paulownia tomentosa* Steud., an extract of Hakukajihi derived from a medicinal plant, an extract of *Ginkgo biloba* L., an extract of Hihatsu derived from a medicinal plant, an extract of *Piper longum* L., an extract of Saishin (*Asiasari radix*) derived from medicinal plant, an extract of *Asiasarum heterotropoides* var. *mandshuricum*, an extract of *Asarum sieboldii* Miq., as well as extracts of spicy plants, such as an extract of tarragon, an extract of dill seeds, an extract of parsley, an extract of turmeric, an extract of nutmeg and the like can be used. These extracts can be prepared using a solvent such as dichloromethane, ethanol, methanol, ethyl ether or the like.

An amount of the above-mentioned additives to be added to a culture medium is as follow. An amount of sesame oil or peanut oil or a total amount of them is 0.001 to 10% by weight per medium, and preferably 0.5 to 10% by weight per medium. An amount of a sesame oil extract and other extract to be added is $3\times10^{-3}$ to $3\times10^{-1}$% by weight per medium. An amount of a dioxabicyclo[3.3.0]octane derivatives such as sesamin, sesaminol, episesamin, episesaminol and the like, or a total amount of a combination thereof is $1\times10^{-3}$ to $1\times10^{-1}$% by weight per medium.

The additive can be added prior to the inoculation of a producer microorganism or immediately after the inoculation. Alternatively, the additive can be added, after the culturing has started, to a culture medium in which the microorganism is growing or has been grown, followed by further culturing. Moreover, the additive can be added both prior to culturing and during culturing after the culturing has started. In the case wherein the additive is added during culturing, the additive can be added once or more than one time, or continuously.

During the culturing, a large amount of lipid containing DGLA is intracellularly accumulated. In the case wherein a liquid medium is used, DGLA is then recovered by a procedure, for example, described in the following.

After the culturing, the cultured cells are recovered by a conventional solid liquid separation means, such as centrifugation or filtering. The cells are thoroughly washed with water, and preferably dried. The drying can be carried out by lyophilization or air drying. The dried cells are extracted with an organic solvent, preferably in a nitrogen gas flow. As an organic solvent, an ether such as ethyl ether, hexane, a lower alcohol such as methanol or ethanol, chloroform, dichloromethane, petroleum ether, or the like can be used. Moreover, an alternating extraction with methanol and petroleum ether, or an extraction with one phase solvent of chloroform-methanol-water can be successfully used. The solvent is distilled off from the extract under reduced pressure to obtain a lipid containing DGLA in a high concentration.

Alternatively, wet cells can be extracted with a solvent miscible with water, such as methanol or ethanol, or a mixed solvent miscible with water, comprising said solvent and water and/or other solvent. Other procedures are the same as described above for dried cells.

The lipid thus obtained contains DGLA as a component of the lipid such as fat. Although DGLA can be directly isolated, preferably it is isolated as an ester with a lower alcohol, for example, as methyl dihomo-γ-linolenate. The esterification accelerates the separation of the target fatty acid from other lipid components, and from other fatty acids produced during the culturing, such as palmitic acid, oleic acid and linoleic acid (these fatty acids are also esterified simultaneously with the esterification of DGLA). For example, to obtain methyl ester of DGLA, the above-mentioned extract is treated with anhydrous methanol/HCl 5 to 10%, or $BF_3$/methanol 10 to 50% at room temperature for 1 to 24 hours.

Methyl ester of DGLA is recovered preferably by extracting the above-mentioned treated solution with an organic solvent such as hexane, an ether such as ethyl ether, or an ester such as ethyl acetate. Next, the resulting extract is dried on, for example, anhydrous sodium sulfate, and the solvent is distilled off preferably under reduced pressure to obtain a mixture comprising fatty acid esters. This mixture contains, in addition to the desired fatty acid HGLA methyl ester, other fatty acid methyl esters, such as methyl parmitate, methyl stearate, methyl oleate and the like. To isolate methyl ester of DGLA from the mixture of these fatty acid methyl esters, column chromatography, low temperature crystallization, the urea-inclusion method, the liquid/liquid countercurrent chromatography method, and the like can be used alone or in combination.

To obtain DGLA from the methyl ester of DGLA, the latter is hydrolyzed with an alkali and freed DGLA is then extracted with an organic solvent, for example, an ether such as an ethyl ether, an ester such as ethyl acetate, or the like.

Moreover, to recover DGLA without using methyl ester, the above-mentioned extracted lipid is subjected to an alkalysis (for example, with 5% sodium hydroxide at room temperature for 2 to 3 hours), and the alkali hydrolysate is extracted and the desired fatty acid DGLA is purified according to a conventional procedure.

EXAMPLES

Next, the present invention is further explained by Examples.

Example 1

100 ml of a medium (pH 6.0) containing 2% glucose and 1% yeast extract was put into a 500 ml Erlenmeyer flask, which was then autoclaved at 120° C. for 20 minutes. *Mortierella alpina* IFO 8568 (Comparative Example) and a mutant SMA 1860 (Example) were separately added to the media, and cultured on a reciprocating shaker (110 rpm) at 28° C. for 6 days. After the culturing the cultured cells were recovered by filtering, washed with water, and lyophilized to obtain 1.28 g of dried cells from the strain IFO 8568, and 1.37 g of dried cells from the mutant SAM 1860.

These cells were extracted with a solvent of one phase chloroform/methanol/water according to Bligh & Dyer extraction method to obtain total lipids in an amount of 505 mg from the strain IFO 8568, and an amount of 530 mg from the mutant SAM 1860. These lipids were subjected to methyl-esterification using anhydrous methanol/hydrochloric acid (95:5) at 50° C. for 3 hours, and the resulting fatty acid methyl esters were extracted to obtain 417 mg of a total fatty acid methyl ester preparation from the strain IFO 8568, and 454 mg of a total fatty acid preparation from the mutant SAM 1860. The fatty acid methyl ester preparations were analyzed by gas chromatography. The result is shown in Table 1.

TABLE 1

|  | Strains | |
| --- | --- | --- |
| Fatty acid | *Mortierella alpina* IFO 8568 | Mutant SAM 1860 |
| Palmitic acid | 0.79 | 0.77 |
| Oleic acid | 0.76 | 0.74 |
| DGLA | 0.20 | 1.27 |
| ARA | 1.42 | 0.46 |
| Total fatty acid | 3.95 | 4.30 |
| Dried cells (g/L) | 12.8 | 13.7 |

The amount of fatty acid is shown in grams per liter medium.

As seen from Table 1, the mutant SAM 1860, whose Δ5 desaturase activity that converts DGLA to ARA is remarkably lowered in comparison with its parent strain, accumulated a large amount of DGLA which is a precursor of ARA. Note, the fatty acid methyl esters were separated by column chromatography to obtain a DGLA methyl ester fraction, which was then analyzed by gas chromatography, high performance liquid chromatography, mass spectrum and NMR analysis. As a result the data conformed to those obtained for a commercial preparation.

Example 2

100 ml of a medium (pH 6.0) containing 2% glucose and 1% yeast extract, a medium (pH 6.0) containing 4% glucose and 1% yeast extract, and a medium (pH 6.0) containing 8% glucose and 1% yeast extract were put into different 500 ml Erlenmeyer flasks, and autoclaved at 120° C. for 20 minutes.

A mutant *Mortierella alpina* SAM 1860 was added to the media, and cultured on a reciprocating shaker (110 rpm) at 28° C. or 20° C. for 10 days. After the culturing, fatty acid methyl ester preparations prepared according to the same procedure as described in Example 1 were analyzed by gas chromatography. The result is shown in Table 2.

TABLE 2

| Culture temperature | Glucose Concentration | Dry cells (g/L) | Yield/medium (g/L) | |
| --- | --- | --- | --- | --- |
|  |  |  | DGLA | ARA |
| 28° C. | 2% | 11.0 | 1.33 | 0.49 |
|  | 4% | 15.5 | 2.49 | 0.99 |
|  | 8% | 20.5 | 3.72 | 1.27 |
| 20° C. | 2% | 11.8 | 1.51 | 0.50 |
|  | 4% | 16.4 | 3.22 | 1.02 |
|  | 8% | 20.0 | 4.10 | 1.20 |

As seen from Table 2, an increase of glucose increased an amount of accumulated DGLA, which is a precursor of ARA. On the other hand, in any case an amount of ARA was suppressed to about 30 to 40% of DGLA. The productivity of DGLA was good at both culture temperatures of 28° C. and 20° C.

Example 3

20 ml of a medium (pH 6.0) containing 2% glucose; 1% yeast extract; 0.2% Tween 20; and 0.5% hydrocarbon, sodium salt of fatty acid, fatty acid ester, or fat or oil, was put into a 100 ml Erlenmeyer flask, and autoclaved at 120° C. for 20 minutes.

A mutant *Mortierella alpina* SAM 1860 was added to each flask, and cultured on a reciprocating shaker (110 rpm) at 28° C. for 7 days. For the resulting cell preparations, fatty acid methyl esters were analyzed by gas chromatography as described in Example 1. The result is shown in Table 3.

TABLE 3

| Additives | Dry cells (g/L) | DGLA (g/L) | ARA (g/L) |
| --- | --- | --- | --- |
| Hexadecane | 18.1 | 1.89 | 0.55 |
| Octadecane | 18.3 | 1.80 | 0.50 |
| Sodium oleate | 15.5 | 1.40 | 0.48 |
| Sodium linoleate | 14.8 | 1.40 | 0.49 |
| Methyl oleate | 18.1 | 1.99 | 0.56 |
| Methyl linoleate | 18.7 | 2.15 | 0.60 |
| Olive oil | 17.9 | 1.92 | 0.59 |
| Cotton seed oil | 18.5 | 1.98 | 0.59 |
| Coconut oil | 18.4 | 1.88 | 0.58 |
| None additive | 13.0 | 1.25 | 0.40 |

When hydrocarbon, sodium salt of fatty acid or oil is added to a basal medium, productivity of DGLA increased by 12 to 72%.

Example 4

5 liters of medium (pH 6.0) containing 2% glucose, 1% yeast extract and 0.1% soybean oil was put into a 5 liter jar fermenter, and after sterilizing at 120° C. for 40 minutes, 200 ml of preculture of a mutant *Mortierella alpina* SAM 1860 was inoculated therein. Culturing was carried out at 28° C. and with aeration at 0.5 v.v.m and agitation for 7 days, and during culturing 150 ml each of 33% glucose solution was added on the second, third, fourth and fifth days.

960 g (dry weight 126 g) of wet cells thus obtained were treated as described in Example 1 to obtain 74.8 g of total lipid and 70.2 g of a fatty acid methyl ester mixture. DGLA content was 30% relating to total fatty acid content, and DGLA productivity was 4.0 g/l, and 165 mg/g dry cells.

Example 5

100 ml each of a medium (pH 6.0) containing 4% glucose and 1% yeast extract was put into 4 Erlenmeyer flasks having a volume of 500 ml, and 0.5 ml each of soybean oil in which sesamin (2,6-bis-(3,4-methylenedioxyphenyl)-cis-3,7-dioxabicyclo[3,3,0]octane) had been dissolved to a sesamin concentration of 15% by weight was added to 2 flasks, and 0.5 ml each of soybean oil was added 2 other flasks, and the flasks were sterilized at 120° C. for 20 minutes.

*Mortierella alpina* IFO 8568 (Comparative Example) was added to two different media, and the mutant SAM 1860 (Example) was add to other different media.

The strains were cultured on a reciprocating shaker (110 rpm) at 28° C. for 7 days. After 24 hours from the start of culturing, 0.5 ml each of the sesamin-containing soybean oil was added to the media to which the sesamin-containing soybean oil had been added, and 0.5 ml each of soybean oil was added to the media to which soybean oil had been added. After culturing, a fatty acid methyl ester preparation was analyzed by gas chromatography as described in Example 1. The result is shown in Table 4.

TABLE 4

| Strains | *M. alpina* IFO 8568 | | Mutant SAM 1860 | |
| --- | --- | --- | --- | --- |
| Addition of sesamin-containing soybean oil | − | + | − | + |
| Ratio of DGLA:ARA | 0.15 | 1.17 | 5.04 | 12.3 |
| Total fatty acid (g/L) | 11.1 | 11.8 | 12.0 | 11.9 |
| Dry cells (g/L) | 23.8 | 24.2 | 24.6 | 24.1 |
| DGLA Productivity (g/L) | 0.39 | 1.87 | 2.45 | 2.93 |

As seen from Table 4, in culturing the strain IFO 8568, even though sesamin which is a Δ5 desaturase inhibitor was added, the ratio of DGLA:ARA did not increase higher than 1.17. On the other hand, in culturing the mutant SAM 1860 whose Δ5 desaturase activity had been decreased, the addition of a Δ5 desaturase inhibitor, sesamin, increased the ratio of DGLA:ARA to 12.3. Note, the addition of sesamin did not effect the amount of total fatty acids produced and the amount of dry cells.

As seen from the above-mentioned results, since it is clear that the production of ARA is suppressed and the production of DGLA is increased, and a ratio of DGLA:ARA is increased by the same effects as described in Japanese Unexamined Patent Publication No 1-243992, then it is clear that besides sesamin, other additives, such as sesame oil, peanut oil, an extract obtained by extracting sesame oil with an organic solvent substantially immissible with sesame oil, an extract of sesame seeds, sesamin, sesaminol, episesamin, episesaminol, sesamolin, 2-(3,4-methylenedioxyphenyl)-6-(3-methoxy-4-hydroxyphenyl)-(3,7-dioxabicyclo[3.3.0] octane, 2,6-bis-(3-methoxy-4-hydroxyphenyl)-3,7-dioxabicyclo[3.3.0]octane, 2-(3,4 -methylenedioxyphenyl)-6-(3-methoxy-4-hydroxyphenoxy)-(3,7-dioxabicyclo[3.3.0] octane, an extract of Gokahi derived from a medicinal plant, an extract of *Acanthopanax gracilistylus* W. W. Smith, an extract of *Acanthopanax senticosus* Harms, an extract of *Acanthopanax henryi*, an extract of *Acanthopanax verticillatus* Hoo, an extract of Touboku derived from a medicinal plant, an extract of *Paulownia fortunei* Hemsl; an extract of *Paulownia tomentosa* Steud., an extract of Hakukajihi derived from a medicinal plant, an extract of *Ginkgo biloba* L., an extract of Hihatsu derived from a medicinal plant, an extract of *Piper longum* L., an extract of Saishin (*Asiasari radix*) derived from medicinal plant, an extract of *Asiasarum heterotropoides* var. *mandshuricum*, an extract of *Asarum sieboldii* Miq., as well as extracts of plants, such as an extract of tarragon, an extract of dill seeds, an extract of parsley, an extract of turmeric, and an extract of nutmeg suppress the production of ARA and increase the production of DGLA, and increase the ratio of DGLA:ARA.

What is claimed is:

1. A process for the production of dihomo-γ-linolenic acid (DGLA) comprising the steps of:

culturing a microorganism of the genus Mortierella having an ability to produce arachidonic acid (ARA) and having reduced or lost Δ5 desaturation activity, so that the microorganism produces DGLA and ARA at a ratio of at least 2.5 (DGLA/ARA) in the absence of Δ5 desaturase inhibitor, in a medium to produce DGLA or a lipid containing DGLA, and recovering the DGLA.

2. A process for the production of a lipid containing DGLA comprising the steps of:

culturing a microorganism of the genus Mortierella having an ability to produce ARA and having reduced or lost 5 desaturation activity in a medium to produce a lipid containing DGLA, so that the microorganism produces DGLA and ARA at a ratio of at least 2.5 (DGLA/ARA) in the absence of Δ5 desaturase inhibitor, and recovering the lipid containing DGLA.

3. A process for the production of DGLA comprising the steps of:

culturing a microorganism of the genus Mortierella having an ability to produce ARA and having reduced or lost Δ5 desaturation activity, so that the microorganism produces DGLA and ARA at a ratio of at least 2.5 (DGLA/ARA) in the absence of Δ5 desaturase inhibitor, in a medium supplemented with a Δ5 desaturase inhibitor, or adding a Δ5 desaturase inhibitor into a medium in which said microorganism has been cultured and further culturing the microorganism to produce DGLA or a lipid containing DGLA, and recovering the DGLA.

4. A process according to claim 3, wherein the Δ5 desaturase inhibitor is a dioxabicyclo[3.3.0]octane derivative represented by the following formula (I):

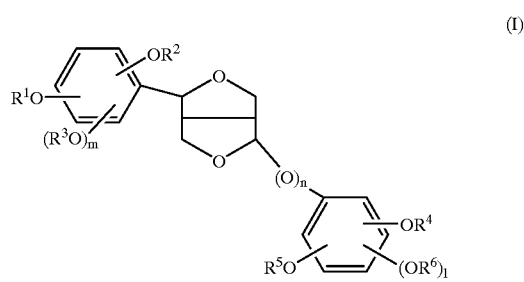

wherein $R^1$, $R^2$, $R^3$, $R^4$, $R^5$ and $R^6$ independently represent a hydrogen atom or an alkyl group having 1 to 3 carbon atoms, or $R^1$ and $R^2$ and/or $R^4$ and $R^5$ together form a methylene group or an ethylene group, and n, m and l are 0 or 1;

piperonyl butoxide, curcumin, or a compound represented by the following formula (II):

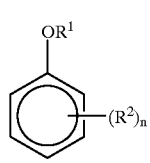

(II)

wherein R¹ represents a lower alkyl group; R² represents a hydroxyl group, an alkyl group, an alkoxy group, an alkenyl group or an oxyalkyl group wherein in the case that more than one R² is present the R² may be the same or different, and n is an integer of 0 to 5.

5. A process according to claim 4, wherein the dioxabicyclo[3.3.0]octane derivative is sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane or 2-(3,4-methylenedioxyphenyl)-6-(3-methoxy-4-hydroxyphenoxy)-3,7-dioxabicyclo[3.3.0]octane.

6. A process for the production of a lipid containing DGLA comprising the steps of:

culturing a microorganism of the genus Mortierella having an ability to produce ARA and having reduced or lost Δ5 desaturation activity, so that the microorganism produces DGLA and ARA at a ratio of at least 2.5 (DGLA/ARA) in the absence of Δ5 desaturase inhibitor, in a medium supplemented with a Δ5 desaturase inhibitor, or adding a Δ5 desaturase inhibitor into a medium in which said microorganism has been cultured and further culturing the microorganism to produce a lipid containing the DGLA, and recovering the lipid containing DGLA.

7. A process according to claim 6, wherein the Δ5 desaturase inhibitor is a dioxabicyclo[3.3.0]octane derivative represented by the following formula (I):

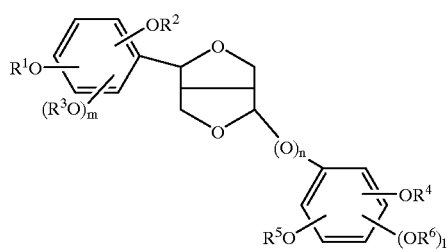

(I)

wherein R¹, R², R³, R⁴, R⁵ and R⁶ independently represent a hydrogen atom or an alkyl group having 1 to 3 carbon atoms, or R¹ and R², and/or R⁴ and R⁵ together form a methylene group or an ethylene group, and n, m and l are 0 or 1;

piperonyl butoxide, curcumin, or a compound represented by the following formula (II):

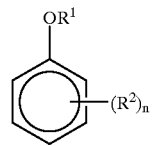

(II)

wherein R¹ represents a lower alkyl group; R² represents a hydroxy group, an alkyl group, an alkoxy group, an alkenyl group or an oxyalkyl group wherein in the case that more than one R² is present, the R² may be the same or different, and n is an integer of 0 to 5.

8. A process according to claim 7, wherein the dioxabicyclo[3.3.0]octane derivative is sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane or 2-(3,4-methylenedioxyphenyl)-6-(3-methoxy-4-hydroxyphenoxy)-3,7-dioxabicyclo[3.3.0]octane.

9. A process for the production of DGLA comprising the steps of:

culturing a microorganism of the genus Mortierella having an ability to produce ARA and having reduced or lost Δ5 desaturation activity, so that the microorganism produces DGLA and ARA at a ratio of at least 2.5 (DGLA/ARA) in the absence of Δ5 desaturase inhibitor, in a medium supplemented with an at least one additive selected from the group consisting of sesame oil, peanut oil, an extract obtained by extracting sesame oil with an organic solvent substantially immiscible with sesame oil, an extract of sesame seeds, an extract of Gokahi derived from a medicinal plant which is *Acanthopanax gracilistylus* W. W. Smith, *Acanthopanax henyri* or *Acanthopanax verticillatus* Hoo, an extract of Touboku derived from a medicinal plant which is *Paulownia fortunei* Hemsl or *Paulownia tomentosa* Steud., an extract of Hakukajihi derived from a medicinal plant which is *Ginkgo biloba* L., an extract of Hihatsu derived from a medicinal plant which is *Piper longum* L., an extract of Saishin (*Asiasari radix*) derived from a medicinal plant which is *Asiasarum heterotropoides* var. *mandshuricum* or *Asarum seiboldii* Miq., an extract of tarragon, an extract of dill seeds, an extract of parsle, an extract of turmeric and an extract of nutmeg, or adding said additive into a medium in which said microorganism has been cultured and further culturing the microorganism to produce DGLA or a lipid containing DGLA, and recovering the DGLA.

10. A process for the production of a lipid containing DGLA comprising the steps of:

culturing a microorganism of the genus Mortierella having an ability to produce ARA and having a reduced or lost Δ5 desaturation activity, so that the microorganism produces DGLA and ARA at a ratio of at least 2.5 (DGLA/ARA) in the absence of Δ5 desaturase inhibitor, in a medium supplemented with at least one additive selected from the group consisting of sesame oil, peanut oil, an extract obtained by extracting sesame oil with an organic solvent substantially immiscible with sesame oil, an extract of sesame seeds, an extract of Gokahi derived from a medicinal plant which is *Acanthopanax gracilistylus* W. W. Smith, *Acanthopanax senticosus* Harms, *Acanthopanax henryi* or

*Acanthopanax verticillatus* Hoo, an extract of Touboku derived from a medicinal plant which is *Paulownia fortunei* Hemsl or *Paulownia tomentosa* Steud., an extract of Hakukajihi derived from a medicinal plant which is *Ginkgo biloba* L., an extract of Hihatsu derived from a medicinal plant which is *Piper longum* L., an extract of Saishin (*Asiasari radix*) derived from a medicinal plant which is *Asiasarum heterotropoides* var. *mandshuricum* or *Asarum seiboldii* Miq., an extract of tarragon, an extract of dill seeds, an extract of parsley, an extract of turmeric and an extract of nutmeg, or adding said additive into a medium in which said microorganism has been cultured and further culturing the microorganism to produce a lipid containing DGLA, and recovering the lipid containing DGLA.

11. The process according to claim 1, wherein the microorganism is *Mortierella alpina* SAM 1860 (FERM BP-3589).

12. The process according to claim 2, wherein the microorganism is *Mortierella alpina* SAM 1860 (FERM BP-3589).

13. The process according to claim 3, wherein the microorganism is *Mortierella alpina* SAM 1860 (FERM BP-3589).

14. The process according to claim 6, wherein the microorganism is *Mortierella alpina* SAM 1860 (FERM BP-3589).

15. The process according to claim 9, wherein the microorganism is *Mortierella alpina* SAM 1860 (FERM BP-3589).

16. The process according to claim 10, wherein the microorganism is *Mortierella alpina* SAM 1860 (FERM BP-3589).

17. The process according to claim 1, wherein the microorganism of the genus Mortierella is of the species of *Mortierella alpina, Mortierella elongata, Mortierella exiqua,* or *Mortierella hygrophila.*

18. The process according to claim 2, wherein the microorganism of the genus Mortierella is of the species of *Mortierella alpina, Mortierella elongata, Mortierella exiqua,* or *Mortierella hygrophila.*

19. The process according to claim 3, wherein the microorganism of the genus Mortierella is of the species *Mortierella alpina, Mortierella elongata, Mortierella exiqua,* or *Mortierella hygrophila.*

20. The process according to claim 6, wherein the microorganism of the genus Mortierella is of the species *Mortierella alpina, Mortierella elongata, Mortierella exiqua,* or *Mortierella hygrophila.*

21. The process according to claim 9, wherein the microorganism of the genus Mortierella is of the species *Mortierella alpina, Mortierella elongata, Mortierella exiqua,* or *Mortierella hygrophila.*

22. The process according to claim 10, wherein the microorganism of the genus Mortierella is of the species of *Mortierella alpina, Mortierella elongata, Mortierella exiqua,* or *Mortierella hygrophila.*

23. The process according to claim 17, wherein the microorganism of the genus Mortierella is of the species *Mortierella alpina.*

24. The process according to claim 18, wherein the microorganism of the genus Mortierella is of the species *Mortierella alpina.*

25. The process according to claim 19, wherein the microorganism of the genus Mortierella is of the species *Mortierella alpina.*

26. The process according to claim 20, wherein the microorganism of the genus Mortierella is of the species *Mortierella alpina.*

27. The process according to claim 21, wherein the microorganism of the genus Mortierella is of the species *Mortierella alpina.*

28. The process according to claim 22, wherein the microorganism of the genus Mortierella is of the species *Mortierella alpina.*

* * * * *